United States Patent
Venu et al.

(10) Patent No.: US 8,945,601 B2
(45) Date of Patent: Feb. 3, 2015

(54) SYSTEM AND METHOD FOR ATTACHING SOFT TISSUE TO AN IMPLANT

(71) Applicants: Purdue Research Foundation, West Lafayette, IN (US); DePuy Products, Inc., Warsaw, IN (US)

(72) Inventors: Perla Venu, West Lafayette, IN (US); Prasanna Malaviya, Fort Wayne, IN (US); Thomas J. Webster, Lafayette, IN (US)

(73) Assignees: DePuy Synthes Products, LLC, Raynham, MA (US); Purdue Research Foundation, West Lafayette, IN (US)

( * ) Notice: Subject to any disclaimer, the term of this patent is extended or adjusted under 35 U.S.C. 154(b) by 85 days.

(21) Appl. No.: 13/660,607

(22) Filed: Oct. 25, 2012

(65) Prior Publication Data

US 2013/0046392 A1 Feb. 21, 2013

Related U.S. Application Data

(63) Continuation of application No. 11/020,587, filed on Dec. 22, 2004, now Pat. No. 8,329,202.

(60) Provisional application No. 60/627,216, filed on Nov. 12, 2004.

(51) Int. Cl.
  *A61F 2/30* (2006.01)
  *A61L 27/32* (2006.01)
  (Continued)

(52) U.S. Cl.
  CPC . *A61F 2/30* (2013.01); *A61L 27/32* (2013.01); *A61L 27/50* (2013.01); *A61L 27/56* (2013.01)
  USPC .......................................................... 424/425

(58) Field of Classification Search
  CPC .... A61K 9/0024; A61K 9/0092; A61L 27/54; A61L 31/16; A61L 2300/604; A61L 2300/624
  See application file for complete search history.

(56) References Cited

U.S. PATENT DOCUMENTS

| 3,906,550 A | 9/1975 | Rostoker et al. |
| 4,352,463 A | 10/1982 | Baker |

(Continued)

FOREIGN PATENT DOCUMENTS

| EP | 0806212 | 11/1997 |
| EP | 1449544 | 8/2004 |

(Continued)

OTHER PUBLICATIONS

Sherwood, J.K. et al. "A Three-Dimensional Osteochondral Composite Scaffold for Articular Cartilage Repair," Biomaterials, Elsevier Science Publishers BV., vol. 23, No. 24, Dec. 2002, pp. 4739-4751.

(Continued)

*Primary Examiner* — Carlos Azpuru
(74) *Attorney, Agent, or Firm* — Barnes & Thornburg LLP

(57) ABSTRACT

One embodiment of the present invention is directed to compositions and methods for enhancing attachment of soft tissues to a metal prosthetic device. In one embodiment a construct is provided comprising a metal implant having a porous metal region, wherein the porous region exhibits a nano-textured surface, and a biocompatible polymer matrix coating the nano-textured surface. The polymer matrix coating comprises a naturally occurring extracellular matrix with biocompatible inorganic materials distributed within the matrix, or a biocompatible polymer and an osteo-inductive agent.

9 Claims, 2 Drawing Sheets

(51) Int. Cl.
*A61L 27/50* (2006.01)
*A61L 27/56* (2006.01)

(56) References Cited

U.S. PATENT DOCUMENTS

| | | | |
|---|---|---|---|
| 4,400,833 A | 8/1983 | Kurland | |
| 4,776,853 A | 10/1988 | Klement et al. | |
| 4,795,436 A | 1/1989 | Robinson | |
| 4,902,508 A | 2/1990 | Badylak et al. | |
| 4,956,178 A | 9/1990 | Badylak et al. | |
| 4,998,239 A | 3/1991 | Strandjord et al. | |
| 5,281,422 A | 1/1994 | Badylak et al. | |
| 5,292,328 A | 3/1994 | Hain et al. | |
| 5,306,311 A | 4/1994 | Stone et al. | |
| 5,354,736 A | 10/1994 | Bhatnagar | |
| 5,372,821 A | 12/1994 | Badylak et al. | |
| 5,415,704 A | 5/1995 | Davidson | |
| 5,445,833 A | 8/1995 | Badylak et al. | |
| 5,516,533 A | 5/1996 | Badylak et al. | |
| 5,554,389 A | 9/1996 | Badylak et al. | |
| 5,573,784 A | 11/1996 | Badylak et al. | |
| 5,635,482 A | 6/1997 | Bhatnagar | |
| 5,641,518 A | 6/1997 | Badylak et al. | |
| 5,645,860 A | 7/1997 | Knapp, Jr. et al. | |
| 5,668,288 A | 9/1997 | Storey et al. | |
| 5,690,670 A | 11/1997 | Davidson | |
| 5,695,998 A | 12/1997 | Badylak et al. | |
| 5,711,969 A | 1/1998 | Patel et al. | |
| 5,730,933 A | 3/1998 | Peterson | |
| 5,733,337 A | 3/1998 | Carr, Jr. et al. | |
| 5,733,868 A | 3/1998 | Peterson et al. | |
| 5,744,515 A | 4/1998 | Clapper | |
| 5,753,267 A | 5/1998 | Badylak et al. | |
| 5,755,791 A | 5/1998 | Whitson et al. | |
| 5,762,966 A | 6/1998 | Knapp, Jr. et al. | |
| 5,788,625 A | 8/1998 | Plouhar et al. | |
| 5,824,651 A | 10/1998 | Nanci et al. | |
| 5,843,741 A | 12/1998 | Wong et al. | |
| 5,866,414 A | 2/1999 | Badylak et al. | |
| 5,885,619 A | 3/1999 | Patel et al. | |
| 5,922,028 A | 7/1999 | Plouhar et al. | |
| 6,056,777 A | 5/2000 | McDowell | |
| 6,077,989 A | 6/2000 | Kandel et al. | |
| 6,099,567 A | 8/2000 | Badylak et al. | |
| 6,106,913 A | 8/2000 | Scardino et al. | |
| 6,129,928 A | 10/2000 | Sarangapani et al. | |
| 6,136,369 A | 10/2000 | Leitao et al. | |
| 6,139,585 A | 10/2000 | Li | |
| 6,143,948 A | 11/2000 | Leitao et al. | |
| 6,171,344 B1 | 1/2001 | Atala | |
| 6,183,255 B1 | 2/2001 | Oshida | |
| 6,214,049 B1 * | 4/2001 | Gayer et al. | 623/16.11 |
| 6,262,017 B1 | 7/2001 | Dee et al. | |
| 6,270,347 B1 | 8/2001 | Webster et al. | |
| 6,291,070 B1 | 9/2001 | Arpac et al. | |
| 6,319,264 B1 | 11/2001 | Tormala et al. | |
| 6,333,029 B1 | 12/2001 | Vyakarnam et al. | |
| 6,344,061 B1 | 2/2002 | Leitao et al. | |
| 6,344,367 B1 | 2/2002 | Naya et al. | |
| 6,355,198 B1 | 3/2002 | Kim et al. | |
| 6,355,699 B1 | 3/2002 | Vyakarnam et al. | |
| 6,368,859 B1 | 4/2002 | Atala | |
| 6,371,985 B1 | 4/2002 | Goldberg | |
| 6,396,208 B1 | 5/2002 | Oda et al. | |
| 6,558,422 B1 | 5/2003 | Baker et al. | |
| 6,569,489 B1 | 5/2003 | Li | |
| 6,572,672 B2 | 6/2003 | Yadav et al. | |
| 6,592,622 B1 | 7/2003 | Ferguson | |
| 6,638,312 B2 | 10/2003 | Plouhar et al. | |
| 6,669,706 B2 | 12/2003 | Schmitt et al. | |
| 6,689,374 B2 | 2/2004 | Chu et al. | |
| 6,736,849 B2 | 5/2004 | Li et al. | |
| 6,756,286 B1 | 6/2004 | Moriceau et al. | |
| 6,790,455 B2 | 9/2004 | Chu et al. | |
| 6,797,514 B2 | 9/2004 | Berenson et al. | |
| 6,805,898 B1 | 10/2004 | Wu et al. | |
| 6,881,249 B2 | 4/2005 | Anderson et al. | |
| 6,929,539 B2 | 8/2005 | Schutz et al. | |
| 2002/0072804 A1 | 6/2002 | Donda | |
| 2002/0167118 A1 | 11/2002 | Billiet et al. | |
| 2002/0173033 A1 | 11/2002 | Hammerick et al. | |
| 2002/0173213 A1 | 11/2002 | Chu et al. | |
| 2003/0040809 A1 | 2/2003 | Goldmann et al. | |
| 2003/0050711 A1 | 3/2003 | Laurencin et al. | |
| 2004/0028875 A1 | 2/2004 | Van Rijn et al. | |
| 2004/0104672 A1 | 6/2004 | Shiang et al. | |
| 2004/0131753 A1 | 7/2004 | Smith et al. | |
| 2004/0153165 A1 | 8/2004 | Li et al. | |
| 2004/0167632 A1 | 8/2004 | Wen et al. | |
| 2004/0167633 A1 | 8/2004 | Wen et al. | |
| 2004/0171323 A1 | 9/2004 | Shalaby | |
| 2004/0241211 A9 | 12/2004 | Fischell et al. | |
| 2006/0173471 A1 | 8/2006 | Carr, Jr. et al. | |

FOREIGN PATENT DOCUMENTS

| | | |
|---|---|---|
| WO | 97/25999 | 7/1997 |
| WO | 97/37613 | 10/1997 |
| WO | 00/16822 | 3/2000 |
| WO | 01/55473 | 8/2001 |
| WO | 03007847 | 1/2003 |
| WO | 03/015836 | 2/2003 |
| WO | 2004/000378 A1 | 12/2003 |

OTHER PUBLICATIONS

European Search Report for European Patent Application No. 05256900.1-1219, Aug. 22, 2007, 10 pgs.
A. Rufai et al., "Journal of Orthopaedic Research," 13:585-593; "Structure and Histopathology of the Insertional Region of the Human Achilles Tendon," (1995).
M. Benjamin et al., "J. Anat," 180: 327-332, "The Structure of the Insertions of the Tendons of Biceps Brachii, Triceps and Brachialis in Elderly Dissecting Room Cadavers," (1992).
P. Frowen et al., "J. Anat." 186 pp. 417-421. "Variations in the Quantity of Uncalcified Fibrocartilage at the Insertions of the Extrinsic Calf Muscles in the Foot," (1995).
J.R. Ralphs et al., "J. Anat," 184 pp. 503-509, "The Joint Capsule: Structure, Composition, Ageing and Disease," (1994).
M. LaBerge et al., "Journal of Biomedical Materials Research," vol. 24, pp. 959-971, Study of Soft Tissue Ingrowth into Canine Porous Coated Femoral Implants Designed for Osteosarcomas Management, (1990).
N. Inoue et al., "Journal of Orthopaedic Research," 20 pp. 957-966, "Biologic Tendon Fixation to Metallic Implant Augmented with Autogenous Cancellous Bone Graft and Bone Morrow in a Canine Model," (2002).
J.D. Bobyn et al., "Journal of Biomedical Materials Research," vol. 16, pp. 571-584, "Effect of Pore Size on the Peel Strength of Attachment of Fibrous Tissue to Porous-Surfaced Implants," (1982).
John Y.J. Yan et al., "Journal of Biomedical Materials Research," vol. 23, pp. 171-189, "Titanium-coated Dacron.RTM. Velour: A Study of Interfacial Connective Tissue Formation," (1989).
J.A. Jansen et al., "Journal of Biomedical Materials Research," vol. 28, pp. 1047-1054, "Tissue Reaction to Soft-Tissue Anchored Percutaneous Implants in Rabbits," (1994).
Y.G.G.K. Paquay et al., "Biomaterials," vol. 17, No. 12, pp. 1251-1256, "Tissue Reaction to Dacron.RTM. Velour and Titanium Fibre Mesh Used for Anchorage of Percutaneous Devices," (1996).
S.A. Hacking et al., John Wiley & Sons, pp. 631-638, "Fibrous Tissue Ingrowth and Attachment to Porous Tantalum," (2000).
F. Gottsauner-Wolf et al., "Acta Orthop Scand." 65 pp. 179-184, "Fixation of Canine Tendons to Metal," (1994).
F. Gottsauner-Wolf et al., "Journal of Orthopaedic Research," 12:814-821, "Tendons Attached to Prostheses by Tendon-Bone Block Fixation: An Experimental Study in Dogs," (1994).
N. Inoue et al., 41st Annual Meeting of the Orthopaedic Research Society, "Fiber Orientation in Soft Tissue Attachment to Metallic Prosthesis," 1 page (1995).

(56) References Cited

OTHER PUBLICATIONS

G.R. Fernie et al, Journal of Biomedical Materials Research, vol. 11, pp. 883-891, "A Percutaneous Implant Using a Porous Metal Surface Coating for Adhesion to Bone and a Velour Covering for Soft Tissue Attachment: Results of Trials in Pigs," (1977).

C.J. Pendegrass et al., "Journal of Orthopaedic Research," 22:1316-1324, "A Histomorphological Study of Tendon Reconstruction to a Hydroxyapatite-Coated Implant: Regeneration of a Neo-Enthesis in Vivo," (2004).

A.S.G. Curtis et al., "Adhesion of cells to polystyrene surfaces," J. Cell Bio., (1983), pp. 1500-1506, 97.

Anthony Atala et al., "Implantation in vivo and retrieval of artificial structures consisting of rabbit and human urothelium and human bladder muscle," J. Ural., (1993), pp. 608-612, 150.

Antonios G. Mikos et al., "Preparation and Characterization of poly(l-lactic acid) foams," Polymer, (1994), pp. 1068-1077, 35(5).

C.B. Wilson et al., "Extracellular matrix and integrin composition of the normal bladder wall," World J. Ural., (1996), pp. S30-S37, 14.

Curtis & Wilkinson, "Review. Topographical control of cells," Biomaterials, (1997), 1573-83, 18(24).

Dee et al., "Design and function of novel osteoblast-adhesive peptides for chemical modification of biomaterials," J. Biomed. Mater. Res., (1998), 371-77, 40.

G.A. Dunn et al., "Alignment of fibroblasts on grooved surfaces described by a simple geometric transformation," J. Cell Sci., (1986), pp. 313-340, 83.

Gunilla Dahlfors et al., "Vascular Endothelial Growth Factor and Transforming Growth Factor-β1 Regulate the Expression of Insulin-Like Growth Factor-Binding Protein-3, -4, and -5 in Large Vessel Endothelial Cells," The Endocrinology Society, (2000), pp. 2062-2067, 141(6).

J. Black and G. Hastings, "Handbook of Biomaterial Properties," (1998), pp. 40-47, Chapman & Hall.

J. Brauker et al., "Neovascularization of immunoisolation membranes: the effect of membrane architecture and encapsulated tissue," Transplant Proce., (1992), p. 2924, 24.

J. Meyle et al., "Variation in contact guidance by human cells on a microstructured surface," J. Biomed. Mater. Res., (1995), pp. 81-88, 29.

Janeta Nikolovski et al., "Smooth muscle cell adhesion to tissue engineering scaffolds," Biomat., (2000), pp. 2025-2032, 21.

Jean-Louis Pariente et al., "In vitro biocompatibility assessment of naturally derived and synthetic biomaterials using normal human urothelial cells," J. Biomed. Mater. Res., (2001), pp. 33-39, 55(1).

Jinming Gao et al., "Surface hydrolysis of poly(glycolic acid) meshes increases the seeding density of vascular smooth muscle cells," J. Biomed. Mat. Res., (1998), pp. 417-424, 42.

John A. Schmidt et al., "Macrophage response to microtextured silicone," Biomat., (1992), pp. 385-389, 12.

Joseph A. Chinn et al., "Enhancement of serum fibronectin absorption and the clonal plating efficiencies of Swiss mouse 3T3 fibroblast and MM14 mouse myoblast cells on polymer substrates modified by radio frequency plasma deposition," J. Colloid Interface Sci., (1989), pp. 67-87, 127.

Jun et al., "An In Vitro Study of Chondrocyte Function on Nanostructured Polymer/Ceramic Formulations to Improve Cartilage Repair," (2002), p. 269, Nano 2002 Conference Abstract Book, Orlando, FL.

Karen M. Haberstroh et al., "The effects of sustained hydrostatic pressure on select bladder smooth muscle cell functions," J. Urol., (1999), pp. 2114-2118, 162.

Kari I. Kivirikko et al., "Modifications of a Specific Assay for Hydroxyproline in Urine," Analytical Biochemistry, (1967), pp. 249-255, 19.

Kay et al., "Nanostructured Polymer Nanophase Ceramic Composites Enhance Osteoblast and Chondrocyte Adhesion," Tissue Engineering, (2002), pp. 753-761, 8(5).

Kenjiro Yamakawa et al., "Peroxisome Proliferator-Activated Receptor-y Agonists Increase Vascular Endothelial Growth Factor Expression in Human Vascular Smooth Muscle Cells," Biochemical and Biophysical Research Communications, (2000), pp. 571-574, 271.

Laurence S. Baskin et al., "Cellular Signaling in the Bladder," www.bioscience.org., Frontiers in Bioscience, (1997), 592-595, 2.

M. Conley et al., "Effects of biodegradable polymer particles on rat marrow-derived stromal osteoblasts in vitro," Biomaterials, (1998), pp. 1255-1268, 19.

M.J. Lydon et al., "Cellular interactions with synthetic polymer surfaces in culture," Biomat., (1985), pp. 396-402, 6.

Malachy J. Gleeson et al., "The use of alloplastic biomaterials in bladder substitution," J. Ural., (1992), pp. 1377-1382, 148.

Mankin et al., "Orthopaedic Basic Science—Chapter 1 Form and Function of Articular Cartilage," American Academy of Orthopaedic Surgeons, (1994), pp. 1-45.

Mark A. Schubert et al., "Role of oxygen in biodegradation of poly(etherurethane urea) elastomers," J. Biomed. Mat. Res., (1997), pp. 519-530, 34.

Miller et al., "An In Vitro Study of Nano-fiber Polymers for Guided Vascular Regeneration," Mat. Res. Soc. Symp. Proce., (2002), pp. 201-204, 711.

Paul Goldhaber, "The influence of pore size on carcinogenicity of subcutaneously implanted Millipore filters," Proc. Am. Assoc. Cancer Res., (1961), p. 228, 3.

Paul Weiss, "In vitro experiments on the factors determining the course of the outgoing nerve fiber," J. Exp. Zool., (1945), pp. 393-448, 68.

Puleo & Bizios, "RGDS tetrapeptide binds to osteoblasts and inhibits fibronectin-mediated adhesion," Bone, (1991), pp. 271-276, 12.

Siegel, "Creating nanophase materials," Scientific American, (1996), p. 74, 275(6).

Susan L. Ishaug-Riley et al., "Human articular chondrocyte adhesion and proliferation on synthetic biodegradable polymer films," Biomaterials, (1999), pp. 2245-2256, 20.

Susan L. Ishaug-Riley et al., "Three-dimensional culture of rat calvarial osteoblasts in porous biodegradable polymers," Biomaterials, (1998), pp. 1405-1412, 19.

Tepper et al., "Nanosized alumina fibers," American Ceramic Society Bulletin, (2001), pp. 57-60, 80(6).

Thapa et al., "An Investigation of Nano-structured Polymers for Use as Bladder Tissue Replacement Constructs," Mat. Res. Soc. Symp. Proc., (2002), pp. 205-210, 711.

Thomas J. Webster et al., "Osteoblast adhesion on nanophase ceramics," Biomaterials, (1999), pp. 1221-1227, 20.

Webster et al., "An in vitro evaluation of nanophase alumina for orthopaedic/dental applications," Bioceramics (Proceedings of the 11th International Symposium on Ceramics in Medicine), (1998), pp. 273-276, 11, LeGeros & LeGeros eds., World Scientific Publishing Co.

Webster et al., "Design and evaluation of nanophase alumina for orthopaedic/dental applications," Nanostructured Materials, (1999), pp. 983-986, 12.

Webster et al., "Enhanced functions of osteoblasts on nanophase ceramics," Biomaterials, (2000), pp. 1803-1810, 21.

Webster et al., "Enhanced surface and mechanical properties of nanophase ceramics to achieve orthopaedic/dental implant efficacy," Key Engineering Materials, (2001), pp. 321-324, 192-195, Proceedings of the 13th International Symposium on ceramics in medicine, Bologna, Italy, Trans Tech Publications.

Webster et al., "Hydroxylapatite with substituted magnesium, zinc, cadmium, and yttrium, II. Mechanisms of osteoblast adhesion," J. Biomed. Mater. Res., (2002), pp. 312-317, 59.

Webster et al., "Mechanisms of enhanced osteoblast adhesion on nanophase alumina involve vitronectin," Tissue Engineering, (2001), pp. 291-301, 7(3).

Webster et al., "Nanoceramic surface roughness enhances osteoblast and osteoclast functions for improved orthopaedic/dental implant efficiency," Scripta Mater., (2001), pp. 1639-1642, 44.

Webster et al., "Specific proteins mediate enhanced osteoblast adhesion on nanophase ceramics," J. Biomed. Mater. Res., (2000), pp. 475-483, 51.

(56) References Cited

OTHER PUBLICATIONS

Young-Jo Kim et al., "Fluorometric Assay of DNA in Cartilge Explants Using Hoechst 33258," Analytical Biochemistry, (1988), pp. 168-176, 174.

Paul Weiss, "Experiments on Cell and Axon Orientation in Vitro: The Role of Colloidal Exudates in Tissue Organization," Journal of Experimental Zoology, (1943), pp. 353-386, 100(3).

Sang-Soo Kim et al., "Poly(lactide-co-glycolide)/hydroxyapatite composite scaffolds for bone tissue engineering," Biomaterials, (2005), pp. 1399-1409, 27.

Gong et al., Titanium oxide nanotube arrays prepared by anodic oxidation, J. Mater. Res., vol. 16, No. 12, Dec. 2001, pp. 3331-3334.

Badylak, S.F. et al. "The Use of Xenogenaic Small Intestinal Submucosa as a Biomaterial for Achille's Tendon Repair in a Dog Model," Journal of Biomedical Materials Research, vol. 29, No. 8, Aug. 1995, pp. 977-985.

\* cited by examiner

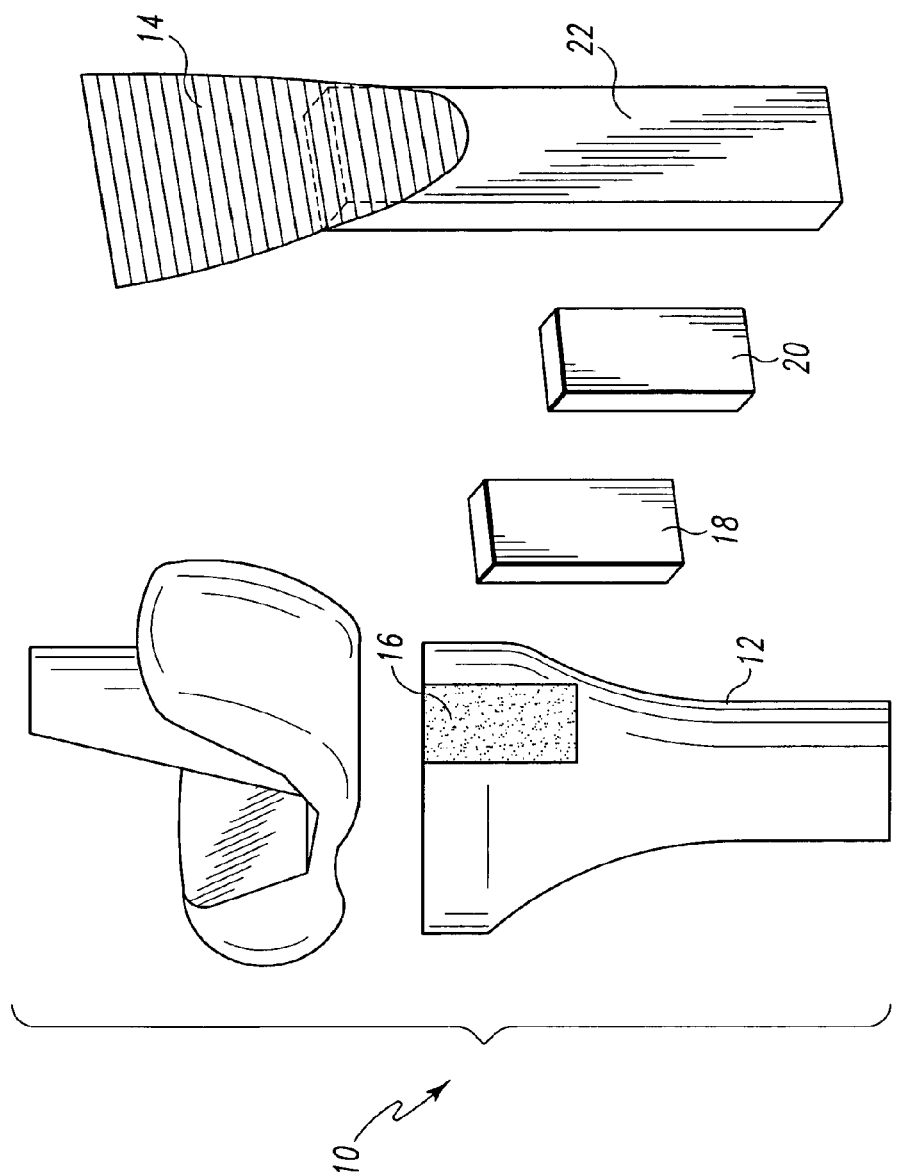

SYSTEM AND METHOD FOR ATTACHING SOFT TISSUE TO AN IMPLANT

CROSS REFERENCE TO RELATED APPLICATIONS

The present application is a divisional application of and claims priority under 35 U.S.C. §120 to U.S. Utility patent application Ser. No. 11/020,587, filed Dec. 22, 2004, which claimed priority under 35 U.S.C. §119(e) to U.S. Provisional Application No. 60/627,216 filed on Nov. 12, 2004, the disclosures of each of which are incorporated herein by reference.

FIELD OF THE INVENTION

The present invention relates to biomedical devices and methods of attaching soft tissues to plastic and metallic prosthesis.

BACKGROUND OF THE INVENTION

Soft connective tissues (e.g. tendons, ligaments, joint capsules) associated with, or spanning, a diarthrodial joint contribute to stabilizing the joint and provide the means for effecting relative motion between the bones. These soft connective tissues have a very unique morphology in terms of their insertion site into bone [Rufai et al., J Orthop Res (1995), 13:585-593; Benjamin et al., J Anat (1992), 180:327-332; Ralphs and Benjamin, J Anat (1994), 184:503-509; Frowen and Benjamin, J Anat (1995), 186:417-421]. As the soft tissue structure approaches its insertion site into bone, the tissue morphology changes from a dense, regular, longitudinally aligned tissue to fibrocartilagenous tissue, to calcified fibrocartilagenous tissue, and finally to bone tissue. Additionally, the collagen fiber orientation changes rapidly from being longitudinal (i.e. along the soft tissue load-bearing direction) to being perpendicular to the calcification tidemark. This uniquely differentiated transition zone at the insertion site is typically referred to as the "enthesis." The normal biology of the soft tissue enthesis (a) ensures a gradual transition from a soft tissue to a much stiffer bone tissue, (b) minimizes mechanical stress concentrations at the attachment site, and (c) maximizes the tendon pullout force from the bone.

Total joint replacement procedures (primary or revision) frequently result in the loss of the attachment site of these soft tissue structures due to osteotomy or simply to gain access to the joint. To fully restore joint function, these soft tissue structures have to be reattached at their anatomical (or equivalent) location around the joint. Such reattachment, however, is a challenging task since it requires mating of two very dissimilar materials i.e. a soft, biological tissue material and a much stiffer, non-biological (metallic or plastic) prosthesis.

One aspect of the present invention is directed to a composition and methodology that recreates the soft tissue enthesis morphology, as found in natural tendon, ligament, and capsular insertion sites, between the metallic implant and the soft tissue structure to be reattached to the metallic implant.

SUMMARY

A composite implant for attaching soft tissues to a plastic or metallic prosthesis and a method of preparing such composite implants comprises one or more of the following features or combinations thereof.

One embodiment of the present invention is directed to a composite implant that upon implantation in vivo regenerates the variously differentiated tissue zones at a tendon attachment site around a diarthrodial joint. This invention will enable soft tissue attachment to a metallic implant, or a metallic surface, by enabling the regeneration of tissues having incrementally increased stiffness including, for example, layers selected from the group consisting of: tendon/ligament/capsular tissue, fibrocartilage tissue, calcified fibrocartilage tissue, bone tissue, metal implant. Hence, the implant of the present invention and the methodologies described herein create a robust connection with high pullout strength between the soft tissue and the implant.

In one embodiment a composite implant is provided for enhancing attachment of a soft tissue to a metal implant, wherein the implant comprises a metal implant having a porous region, wherein said porous region exhibits a nano-textured surface, and a calcified material layer coating the nano-textured surface. In one embodiment the average maximum height of the protrusions comprising the nano-textured surface is selected from a range of about 50 nm to about 200 nm. The nanotextured surface can be prepared using standard techniques including anodization of the metal surface or by chemical etching of the metal surface.

In one particular embodiment a construct for enhancing the attachment of soft tissue to a metal implant is provided. The construct comprises a metal implant comprising a porous region, wherein said porous region exhibits a nano-textured surface, and a biocompatible polymer matrix coating the nano-textured surface, wherein the biocompatible polymer matrix comprises a naturally occurring extracellular matrix and an exogenous biocompatible inorganic material. In one aspect of the present invention the naturally occurring extracellular matrix comprises intestinal submucosa in gel form, and the biocompatible inorganic material is dispersed within the intestinal submucosa. The exogenous biocompatible inorganic material in accordance with one embodiment comprises hydroxyapatite and in a further embodiment the gelled intestinal submucosa is coated onto the nano-textured surface and dried. In an alternative embodiment the biocompatible polymer matrix comprises a biocompatible polymer and an exogenously added osteo-inductive agent, and optionally, exogenously added hydroxyapatite.

In one embodiment the composite implant further comprises an extender layer coupled to a metal implant and in contact with a biocompatible polymer matrix present on the metal implant, wherein said extender layer comprises a submucosal matrix, and a synthetic portion coupled to the submucosal matrix. More particularly the synthetic portion comprises a mesh member wherein said mesh member is coated with a comminuted naturally occurring extracellular matrix.

In another embodiment a composite bioprosthetic construct is provided. In this embodiment the construct comprises a metal implant that comprises a porous region, wherein said porous region exhibits a nano-textured surface, a calcified material layer coating the nano-textured surface; and a scaffold layer comprising a biocompatible polymer matrix and growth factors, wherein at least a portion of said scaffold layer is in contact with said calcified material layer. In one embodiment the calcified material layer comprises hydroxyapatite and a biocompatible polymer matrix, and optionally an exogenously added osteo-inductive agent. In one embodiment the calcified material layer comprises a naturally occurring extracellular matrix, including for example a submucosal matrix. In a further embodiment an extender layer coupled to the scaffold layer of the construct, wherein the extender layer comprises a submucosal matrix, and a synthetic portion coupled to the submucosal matrix.

The present invention also encompasses kits for repairing joints and attaching soft tissues to prosthesis. In one embodiment a kit for repairing a diarthrodial joint comprises a metal implant comprising a porous region, wherein the porous region exhibits a nano-textured surface, a biocompatible polymer matrix coating the nano-textured surface, wherein the biocompatible polymer matrix comprises a naturally occurring extracellular matrix and exogenously added biocompatible inorganic material, and an extender graft comprising a naturally occurring extracellular matrix, and a mesh member coupled to the naturally occurring extracellular matrix. In accordance with one embodiment the biocompatible inorganic material comprises nano-scale hydroxyapatite crystals.

The present invention is also directed to a method of attaching soft tissue to a metal implant. In one embodiment the method comprises the steps of first providing a metal implant construct, wherein said construct comprises 1) a metal implant comprising a porous region that exhibits a nano-textured surface, and 2) a biocompatible polymer matrix coating the nano-textured surface, wherein the biocompatible polymer matrix comprises a naturally occurring extracellular matrix and an exogenously added biocompatible inorganic material. At least a portion of a scaffold layer is then coupled to the metal implant construct in a manner that places it in contact with the biocompatible polymer matrix. In one embodiment the scaffold layer comprises a biocompatible polymer matrix and a growth factor. The proximal end of an extender portion is then attached to the scaffold layer, wherein said extender portion comprises a submucosal matrix, and a synthetic portion coupled to the submucosal matrix and attaching the distal end of the extender portion to a patient's soft tissue. In one embodiment the synthetic portion comprises a mesh member wherein said mesh member is coated with a naturally occurring extracellular matrix.

BRIEF DESCRIPTION OF THE DRAWINGS

FIG. 2 represents a schematic drawing of a diarthrodial joint prosthesis and a composite implant for soft tissue enthesis regeneration. The metal implant (10) comprises a tibial component (12) of a knee joint prosthesis and the soft tissue to be attached is a ligament or tendon (14). The metal implant is provided with a porous region, the surface of which is provided with a nano-textured roughness (16). The nano-textured surface is coated with a calcified matrix (18) and the calcified matrix is bound to a scaffold layer (20) that comprises a bioactive uncalcified matrix. The scaffold layer is coupled to an extender (22) that is in turn attached to a ligament or tendon (14).

DETAILED DESCRIPTION

Definitions

Figure 1:
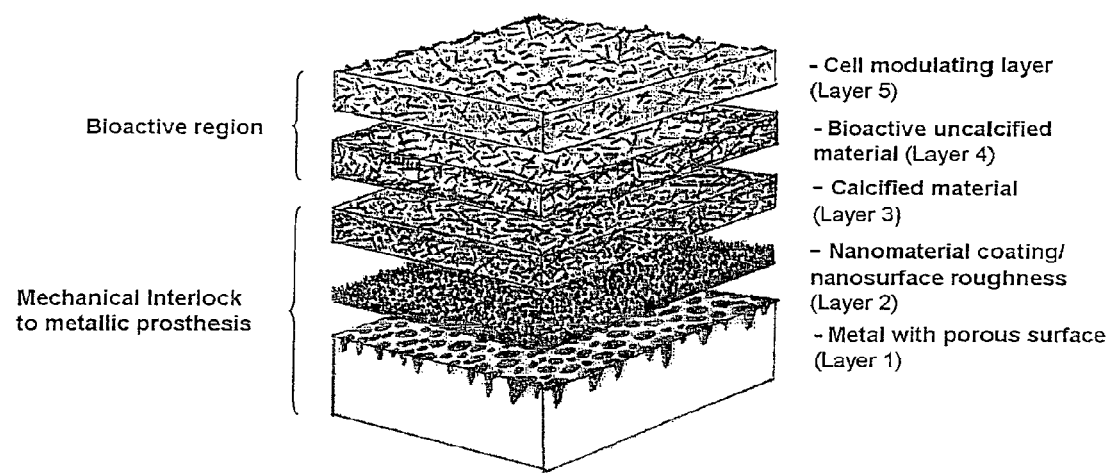
FIG. 1 represents a schematic drawing of a composite implant for soft tissue enthesis regeneration. The composite implant of this embodiment comprises five layers, with layers 1-3 representing the materials and/or surface treatments which, upon implantation of the composite, will regenerate calcified tissue which is mechanically interlocked with the implant surface, and layers 4 and 5 representing materials which, upon implantation of the composite, will bind the patient soft tissue to the mechanically-interlocked calcified tissue. Individually, the layers are as follows: layer 1 represents the metal implant comprising a porous surface region; layer 2 represents a nano-textured surface layer; layer 3 represents a calcified matrix; layer 4 represents a bioactive uncalcified matrix and layer 5 represents a cell modulating layer.

In describing and claiming the invention, the following terminology will be used in accordance with the definitions set forth below.

As used herein the term "bioactive agents" includes one or more of the following: growth factors selected from the group consisting of members of the transforming growth factor-beta (TGF-b) superfamily, such as members of the bone morphogenetic protein (BMP) family (including BMP-2, BMP-4, BMP-6, BMP-12, and BMP-14 and ADMP) and members of the growth and differentiation factor (GDF) family (including GDF4, GDF5, GDF6, GDF7, and GDF8); members of the fibroblast growth factor (FGF) family; members of the insulin-like growth factor (IGF) family; members of the platelet-derived growth factor family (PDGF); members of the epidermal growth factor (EGF) family; angiogenic growth factors such as vascular endothelial growth factors (VEGF); cytokines such as members of the interleukin (IL) family and colony stimulating factors (CSF); proteins such as members of the hedgehog family of proteins, members of the parathyroid hormone (PTH) and PTH-related family of proteins (PTHrPs); skeletal tissue extracellular matrix components such as proteoglycans, glycosaminoglycans, hyaluronic acid, chondroitin sulfate, decorin, dermatan sulfate, keratan sulfate, tenascin, fibronectin, vitronectin, and bone sialoprotein; other factors such as thromboelastin, thrombin, heparin, various ligands, and members of the integrin family; small peptides that modulate cell attachment such as RDG peptides, small peptide collagen analogues (see U.S. Pat. Nos. 5,354, 736 and 5,635,482, the disclosures of which are incorporated herein), small peptide fibronectin analogues, small peptide bone sailoprotein analogues, integrin-binding domains, and heparin-binding domains; small peptides that effect the upregulation of specific growth factors such as thrombin-derived peptides (e.g. Chrysalin, available from Chrysalis BioTechnology and Orthologic Corp). Additionally, the term "bioactive agents" also includes therapeutic drugs (such as antibiotics, antimicrobials, steroidal and non-steroidal analgesic and anti-inflammatory drugs, anti-rejection agents such as immune-suppressants and anti-cancer drugs) or other therapeutic agents that can directly effect gene regulation such as DNA, DNA fragments, or DNA plasmids, RNA, RNA fragments, micro RNAs (miRNAs), and short double-stranded RNA for post-translational RNA interference (RNAi).

As used herein the term "biologically derived agents" include one or more of the following: bone (autograft, allograft, and xenograft) and derivates of bone; cartilage (autograft, allograft, and xenograft), including, for example, meniscal tissue, and derivatives; ligament (autograft, allograft, and xenograft) and derivatives; derivatives of intestinal tissue (autograft, allograft, and xenograft), including for example submucosa; derivatives of stomach tissue (autograft, allograft, and xenograft), including for example submucosa; derivatives of bladder tissue (autograft, allograft, and xenograft), including for example submucosa; derivatives of alimentary tissue (autograft, allograft, and xenograft), including for example submucosa; derivatives of respiratory tissue (autograft, allograft, and xenograft), including for example submucosa; derivatives of genital tissue (autograft, allograft, and xenograft), including for example submucosa; derivatives of liver tissue (autograft, allograft, and xenograft), including for example liver basement membrane; derivatives of skin tissue; platelet rich plasma (PRP), platelet poor plasma (PPP), bone marrow aspirate, demineralized bone matrix, whole blood, fibrin, and blood clot. Purified ECM and other collagen sources are also intended to be included within "biologically derived agents."

As used herein the term "cells", absent any further elaboration or characterization, includes one or more of the following: chondrocytes; fibrochondrocytes; osteocytes; osteoblasts; osteoclasts; synoviocytes; bone marrow cells; mesenchymal cells; stromal cells; stem cells; embryonic stem cells; precursor cells derived from adipose tissue; peripheral blood progenitor cells; stem cells isolated from adult tissue; genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. If other cells are found to have therapeutic value in the orthopaedic field, it is anticipated that at least some of these cells will have use in the present invention, and such cells should be included within the meaning of "cell" and "cells" unless expressly limited otherwise. Illustratively, in one example of embodiments that are to be seeded with living cells such as osteoblasts, a sterilized implant may be subsequently seeded with living cells and packaged in an appropriate medium for the cell type used. For example, a cell culture medium comprising Dulbecco's Modified Eagles Medium (DMEM) can be used with standard additives such as non-essential amino acids, glucose, ascorbic acid, sodium pyruvate, fungicides, antibiotics, etc., in concentrations deemed appropriate for cell type, shipping conditions, etc. Alternatively, the living cells can be derived from a mammalian patient at the point-of-care and combined with one or more elements of a composite implant prior to implantation.

As used herein the term "biocompatible polymers" is intended to include both synthetic polymers and biopolymers (e.g. collagen), and a "biocompatible polymer matrix" refers to a mass formed by such polymers. Examples of biocompatible synthetic polymers include: polyesters of [alpha]-hydroxycarboxylic acids, such as poly(L-lactide) (PLLA) and polyglycolide (PGA); poly-p-dioxanone (PDO); polycaprolactone (PCL); polyvinyl alcohol (PVA); polyethylene oxide (PEO); polymers disclosed in U.S. Pat. Nos. 6,333,029 and 6,355,699; co-polymer or a mixture of polymers and/or co-polymers such as polymer networks of poly(acrylamide-co-ethylene glycol/acrylic acid) or poly(lysine-(lactide-ethylene glycol)) or any other biocompatible polymer, co-polymer or mixture of polymers or co-polymers that are utilized in the construction of prosthetic implants or prosthetic implant coatings. Examples of commercially available synthetic biocompatible polymers include Prolene™, Vicryl™, Mersilene™, and Panacryl™. In addition, as new biocompatible, bioresorbable materials are developed, it is expected that at least some of them will be useful materials from which orthopaedic devices may be made. It should be understood that the above materials are identified by way of example only, and the present invention is not limited to any particular material unless expressly called for in the claims.

As used herein the term "biocompatible inorganic materials" include materials such as hydroxyapatite, all calcium phosphates, alpha-tricalcium phosphate, beta-tricalcium phosphate, calcium carbonate, barium carbonate, calcium sulfate, barium sulfate, polymorphs of calcium phosphate, sintered and non-sintered ceramic particles, and combinations of such materials. Additionally, "biocompatible inorganic materials" also include salts of di- or tri-valent metal cations such as copper, iron, manganese, and magnesium with anions such as, for example, chlorides and sulfates.

As used herein the term "collagen-based matrix" refers to extracellular matrices that comprise collagen fibers and include both naturally occurring extracellular matrices as well as reconstituted collagen matrices.

As used herein the term "naturally occurring extracellular matrix" includes isolated natural extracellular matrices (such as intestinal submucosa) in their native configuration, from a mammalian organ body wall (such as, for example, stomach wall, intestinal wall, bladder wall, liver or lung basement membrane), as well as natural extracellular matrix material that has been subjected to delamination, comminution, fluidization, and gelation. However, it is not within the definition of a naturally occurring extracellular matrix to extract and purify the natural fibers and refabricate a matrix material from purified natural fibers. Such a refabricated matrix is referred to as a "reconstituted collagen matrix" or "reconstituted ECM matrix".

As used herein the term "submucosal matrices" refers to natural extracellular matrices, known to be effective for tissue remodeling, that have been isolated in their native configuration.

As used herein the term "exogenous" or "exogenously added" designates the addition of a new component to a composition, or the supplementation of an existing component already present in the composition, using material from a source external to the composition.

As used herein the term "calcification-inducing layer" or like terms relate to a composition of matter that comprises agents that actively induce the calcification of the composition when the composition is implanted in a patient.

As used herein the term "apatite" refers to minerals defined by the general formula: $A_5(B)_3$ (OH, F, Cl or $CO_3$), wherein the A component of the formula represents a metal cation selected from the group consisting of calcium, barium, strontium, and cerium. The B component can be either a phosphate ($PO_4$) or carbonate ($CO_3$) anion groups.

As used herein the term "fluidized matrices" and like terms, encompass collagen-based matrices (including for example intestinal submucosa) that have been modified to allow the material, at room temperature, to flow and conform to the shape of its container.

As used herein the term "gelled matrices" and like terms, encompass collagen-based matrices (including for example intestinal submucosa) that have been modified to exhibit the properties of a jelly (i.e. a viscous material that generally maintains its shape, but is capable of being molded to different shapes) at room temperature.

Embodiments

One aspect of the present invention is directed to a novel composite implant and method for regenerating soft tissue enthesis. The composite system is composed of different biologic or non-biologic materials wherein the composite system is interposed between soft tissue and a metallic or hard plastic prosthesis. After insertion into a patient, the composite system is remodeled over time to regenerate a differentiated transition zone of attachment that is biologically similar to the naturally occurring transition zone of attachment of a soft tissue to bone in the vicinity of a diarthrodial joint. Accordingly, the novel composite implants of the present invention can be used to attach tendons, ligaments, joint capsules, and other soft tissue to metallic or plastic implants to minimize the mechanical stress concentrations at the attachment site and maximize the soft tissue pull out force from the prosthetic implant.

In accordance with one embodiment the composite implant comprises two main regions: the mechanical interlock region and the bioactive region. The mechanical interlock region comprises relatively hard and stiff composites and functions to regenerate calcified tissue which is mechanically interlocked with the porous texture at the implant surface. This regenerated, mechanically-interlocked calcified tissue provides a strong attachment to the metallic implant. The bioactive region comprises softer composites, and functions to connect the calcified tissue of the mechanical interlock region to soft tissue, such as a tendon, ligament, or joint capsule.

The mechanical interlock region binds non-metal calcified material with the metal surface by promoting bone regeneration and ingrowth into the metal. In accordance with one embodiment, three layers contribute to the functionality of the mechanical interlock region. The first layer comprises a porous metal surface, the second layer is a nano-material layer that provides nano-surface roughness, and the third layer comprises a calcified or calcification-inducing layer.

Techniques for producing metallic implants that comprise a porous region are known to those skilled in the art and include the use of metal (i.e. titanium) plasma sprays, metallic bead coatings (i.e. Porocoat® Porous Coating), the attachment of a porous fiber mesh material, (such as the type described in Rostoker, et al's U.S. Pat. No. 3,906,550), a reticulated metallic porous material with interconnected pores (such as, for example, Trabecular Metal® or Hedrocel®) or other metallic porous material. In accordance with one embodiment the metal implant is provided with a porous region comprising a Porocoat® Porous Coating. In this embodiment the coating is composed of a powder of nearly spherical, metallic beads of approximately 150 μm to 300 μm in diameter that are adhered to the desired location on the metal implant by, for example, a sintering process. This technique results in a multi-layered, beaded coating that is open, with interconnected pores, and extremely rough, and provides a strong initial fixation upon implantation. The density of pores is inversely related to diameter of spherical metallic beads used for coating the metallic implant. In one embodiment the average value porosity of the porous regions is somewhere in the range of about 30% to about 80%. In one embodiment the average value porosity of the porous regions is somewhere in the range of about 70% to about 80%. In another embodiment the average value porosity of the porous regions is somewhere in the range of about 40% to about 50%. In another embodiment average value porosity of the porous regions is somewhere in the range of about 30% to about 35%. In one embodiment the coating has a graded density, increasing in porosity near the outer surface and increasing in density and strength near the implant surface. In one embodiment the maximum diameter of the pores ranges from about 10 μm to about 800 μm in size. In another embodiment the maximum diameter of the pores ranges from about 100 μm to about 400 μm. This size is sufficient for ingrowth of bone, yet the spheres are small enough to provide a rough surface. In one embodiment the pores are randomly distributed across the porous region and the pores have an irregular shape.

In accordance with one embodiment, the surface of the porous region is modified to exhibit a nano-textured surface. This can be accomplished by either adhering nanoparticles to the metal surface of the porous region or by etching the original surface to provide a nanotexture. As defined herein a nano-textured surface relates to a surface that has been roughened to exhibit a series of cavities and protrusions wherein the maximum distance from the highest point to the lowest point on the porous region is less than 200 nanometers. In one embodiment the average height of the protrusions ranges anywhere from about 20 nm to about 200 nm, and in one embodiment the average height of the protrusions ranges anywhere from about 30 nm to about 120 nm, in another embodiment the average height of the protrusions ranges anywhere from about 40 nm to about 100 nm and in another embodiment the average height of the protrusions is less than 100. In one embodiment the nano-textured surface comprises a series of protrusions wherein the minimum height of the protrusions is 50 nm and the maximum height of the protrusions is about 150 nm as measured from the lowest point on the porous region. In one embodiment the protrusions are irregularly shaped and distributed randomly on the textured surface. The distance between protrusions (as measured from the center of one protrusion to the center of its neighbor) can range anywhere from about 25 nm to about 500 nm, and in one embodiment the average distance between protrusions of the nano-textured surface is a value selected from the range of about 50 nm to about 250 nm In accordance with one embodiment a metallic implant device is prepared that comprises a porous region, wherein the metallic implant device is further modified to display a nanosurface roughness on the device, at least on the area that includes the porous region. In one embodiment the nanosurface roughness on the implant surface is prepared by anodization at low voltage for short period. For example, anodization of metallic surfaces (Ti metal or Ti-6Al-4V alloy) at 20 volts for 1, 3 and 5 minutes after pretreatment of the samples with an acid mixture (2 ml of 48% HF+3 ml of 70% $HNO_3$ in 100 ml of DI water) produces a nanosurface roughness in accordance with the present invention. Nano-roughness can also be achieved via other means such as chemical etching or adhering nano particles to the metal surface of the device. Additional methods of preparing a nanosurface topography are described in U.S. Pat. Nos. 6,136,369, 6,143,948 and 6,344,061 as well as published US applications US 20040167632 and US 20040167633, the disclosures of which are incorporated herein. The nanosurface roughness mimics the jigsaw-like interlocking between calcified fibrocartilage and bone in the natural entheses.

Within the mechanical interlock region, the nanosurface roughened area is in contact with a calcified material layer or a calcification inducing layer. In one embodiment the calcified material layer consists of a pure hydroxyapatite/calcium containing mineral. In another embodiment the calcified material layer comprises a biocompatible polymer matrix and a hydroxyapatite/calcium containing mineral layer formed either as two or more discrete layers or as a mixture of the mineral and polymer. In another embodiment the calcified material layer comprises a mixture of a hydroxyapatite/calcium containing mineral and a biocompatible polymer matrix. In accordance with one embodiment cycles of alternative pressure and suction is be applied to fill the porocoat structure on the metallic implant with gel or fluidized form of natural extracellular matrix or collagen-based matrices.

In one embodiment the calcification-inducing layer of the mechanical interlock region comprises a biocompatible polymer matrix that is bound to, or entraps within the matrix, bioactive agents that actively induce the calcification of this tissue. In accordance with one embodiment the biocompatible polymer matrix is selected from the group consisting of natural and reconstituted collagen matrices, and naturally occurring extracellular matrices, including submucosal matrices. Extracellular matrices isolated from various tissues are known to be effective for tissue remodeling, and include, but are not limited to, extracellular matrices isolated from mammalian intestine, stomach, bladder, alimentary, respiratory, and genital submucosa. See, e.g., U.S. Pat. Nos. 4,902,508, 6,171,344, 6,099,567, and 5,554,389, the disclosures of which are hereby incorporated by reference. These tissues are referred to generally as "submucosal matrices" and comprise highly conserved collagens, glycoproteins, proteoglycans, and glycosaminoglycans. Additionally, other known extracellular matrices, for example lamina propria and stratum compactum, may also be used in accordance with the present invention.

In one embodiment the calcified material layer/calcification-inducing layer comprises intestinal submucosa, and in one embodiment the layer comprises small intestinal submucosa of a warm blooded vertebrate. In one embodiment, the material comprises the tunica submucosa along with the lamina muscularis mucosa and the stratum compactum of a segment of intestine, said layers being delaminated from the tunica muscularis and the luminal portion of the tunica mucosa of said segment. Such a material is referred to herein as intestinal submucosa (SIS). In accordance with one embodiment of the present invention the intestinal submucosa comprises the tunica submucosa along with basilar portions of the tunica mucosa of a segment of intestinal tissue of a warm-blooded vertebrate. While porcine SIS is widely used, it will be appreciated that intestinal submucosa may be obtained from other animal sources, including cattle, sheep, and other warm-blooded mammals.

The preparation of SIS from a segment of small intestine is detailed in U.S. Pat. No. 4,902,508, the disclosure of which is expressly incorporated herein by reference. A segment of intestine is first subjected to abrasion using a longitudinal wiping motion to remove both the outer layers (particularly the tunica serosa and the tunica muscularis) and the inner layers (the luminal portions of the tunica mucosa). Typically the SIS is rinsed with saline and optionally stored in a hydrated or dehydrated state until use. Currently there are multiple patents and publications that describe in detail the characteristics and properties of intestinal submucosa (SIS). See, for example, U.S. Pat. Nos. 4,352,463, 4,902,508, 4,956,178, 5,281,422, 5,372,821, 5,445,833, 5,516,533, 5,573,784, 5,641,518, 5,645,860, 5,668,288, 5,695,998, 5,711,969, 5,730,933, 5,733,868, 5,753,267, 5,755,791, 5,762,966, 5,788,625, 5,866,414, 5,885,619, 5,922,028, 6,056,777, and WO 97/37613, the disclosure of which is incorporated herein by reference. SIS, in various forms, is commercially available from Cook Biotech Incorporated (Bloomington, Ind.), DePuy Orthopaedics (Warsaw, Ind.), and Biomet, Inc. (Warsaw, Ind.). Further, U.S. Pat. No. 4,400,833 to Kurland and PCT publication having International Publication Number WO 00/16822 provide information related to bioprosthetics and are also incorporated herein by reference.

Naturally occurring extracellular matrices can be prepared as "fluidized forms" comprising solutions or suspensions of the matrix by comminuting and/or digesting the matrix with a protease, such as trypsin or pepsin, or by an acid (such as, for example, ascetic acid) for a period of time sufficient to solubilize said tissue and form a substantially homogeneous solution or suspension. In one embodiment an intestinal submucosa matrix is used as the starting material, and the material is comminuted by tearing, cutting, grinding, shearing and the like. In one embodiment, the intestinal submucosa is ground in a frozen or freeze-dried state to prepare a comminuted form of SIS. This grinding process produces a fine powder-like comminuted SIS upon drying. Alternatively, comminuted SIS can also be obtained by subjecting a suspension of pieces of the submucosa to treatment in a high speed (high shear) blender, and dewatering, if necessary, by centrifuging and decanting excess water to produce finely comminuted SIS fibers. The comminuted submucosa fibers can be dried and further ground to form a submucosa powder. Thereafter, it can be hydrated, that is, combined with water or buffered saline and optionally other pharmaceutically acceptable excipients to form a tissue graft composition as a fluid having a viscosity of about 2 to about 300,000 cps at 25° C. Higher viscosity graft compositions having a gel or paste consistency, can be prepared from the SIS solutions/suspensions by adjusting the pH of such solutions/suspensions to about 6.0 to about 7.0. The present compositions can be sterilized using art-recognized sterilization techniques such as exposure to ionizing radiation.

Alternatively, in one embodiment gelled submucosa matrices are prepared through the use of heat to dissemble the collagen-based material followed by cooling the material. In accordance with one embodiment naturally occurring extracellular matrices or even pure collagen can be formed as a gel by subjecting the material to temperatures ranging from about 30° C. to about 70° C. for a predetermined length of time. In one embodiment the material is heated at about 30° C. to about 60° C. for 10 to 20 minutes, and in one embodiment the material is heated at 60° C. for 20 minutes. The material is then allowed to cool, typically to room temperature to form the submucosa gel. Use of fluidized, gelatinized, or heated collagen-based extracellular matrices (such as SIS) for coating orthopaedic implants not only enhances the uniformity of coating, by reducing uncoated gaps on the surface, but it also enhances the interlocking properties of the material. For example, the use of gelled SIS material enhances the interlocking properties of the intestinal submucosa 3 to 4 fold. This also prevents loss of the coating during handling and transportation.

In one embodiment the calcified material layer comprises a naturally occurring extracellular matrix that is modified to include one or more exogenously added bioactive agents or biocompatible inorganic materials. In one embodiment the calcified material layer comprises a naturally occurring extracellular matrix that is modified to include exogenously added apatite. In one embodiment the exogenously added apatite includes compounds of the formula: $Ca_5(PO_4)_3$ (OH, F, Cl or $CO_3$). Examples of other suitable biocompatible inorganic materials for use in the present invention include: hydroxyapatite, all calcium phosphates, alpha-tricalcium phosphate, beta-tricalcium phosphate, calcium carbonate, barium carbonate, calcium sulfate, barium sulfate, polymorphs of calcium phosphate, ceramic particles, and combinations of such materials. In accordance with one embodiment the added biocompatible inorganic material is hydroxyapatite. In one embodiment the hydroxyapatite is in particulate form (having a mean diameter of less than 500 nm, or less than 250 nm or less than 150 nm), wherein the particles are dispersed on the surface and/or within the extracellular matrix.

Sonication of conventional hydroxyapatite (HA) powders (having particles with a mean diameter in the micron range) in water for 6 hours provides nano-HA dispersions. This treatment stabilizes HA dispersions in water, and the dispersions remained stable for several days to weeks after sonication treatment. Mean particle diameters of the dispersions made out of conventional HA powders were 1.678 µm with approximately 50% of the particles having diameters less than 1.5 µm. Whereas, the corresponding values for sonicated HA were 0.118 µm with approximately 50% of the particles having diameters less than 0.098 µm. Further, X-ray diffraction analysis suggests that the crystalline phases of HA are not affected by aqua-sonication. In accordance with one embodiment, the HA is hydrothermally treated (for example at about 200° C. for 20 hours under pressure) and then sonicated for 2 hours to provide nano-HA dispersions. Mean particle diameters of nano-hydroxyapatite dispersions produced by this method were about 86.75 nm with approximately 50% of the particles having diameters less than about 83.50 nm. A complete surface coating on implants can be achieved with nano-HA dispersions.

In one embodiment the nano-textured surface is coated with a calcified material layer that comprises a biocompatible polymer and a biocompatible inorganic material. The biocompatible polymer may comprise a natural or reconstituted collagen matrix and may be selected from a naturally occurring extracellular matrix. In one embodiment the calcified material layer comprises a collagen matrix and nano-scale hydroxyapatite crystals, wherein said crystals are entrapped or bound to the collagen matrix material.

In accordance with one embodiment a calcified material layer is provided as the third layer of the mechanical interlock region, wherein the calcified material layer comprises a naturally occurring extracellular matrix and hydroxyapatite. In one embodiment the calcified material layer comprises a naturally occurring extracellular matrix in fluid or gel form combined with nanoparticulate hydroxyapatite (HA). In one embodiment the calcified material layer comprises gelled intestinal submucosa and nanoparticulate HA, wherein the nanoparticulate HA is dispersed within the gelled submucosa matrix and the matrix is coated onto the nano-textured surface and dried. Preparation of emulsions with SIS powder and nanoparticulate HA in dispersion form @ about a 1:0.25 ratio of SIS to HA (dry weight %) followed by gelatinization at 60° C. for 20 minutes provides an effective coating that not only mimics the natural entheses (i.e., attachment site between implant and tendon/soft tissues) tissues but also enhances the interlocking characteristics of SIS on metals. Further, fibrous collagen-based foam scaffolds with nano- or micro-scale HA crystals deposited on the fibers can be used (e.g. mineralized SIS, DePuy Spine's Healos®). The calcified material layer can also contain exogenously added bioactive agents, biologically derived agents, cells, or other biocompatible inorganic materials. In one embodiment the calcified material layer comprises a biocompatible inorganic material selected form the group consisting of copper (II) sulfate pentahydrate ($CuSO_4.5H_2O$), copper (II) chloride hydrate ($CuCl_2.2H_2O$), iron-dextran, iron (II) sulfate heptahydrate ($FeSO_4.7H_2O$), manganese (II) sulfate monohydrate ($MnSO_4, H_2O$), magnesium sulfate heptahydrate ($MgSO_4. 7H_2O$), magnesium phosphate dibasic trihydrate ($MgHPO_4.3H_2O$), glycine, proteoglycans, Vit A, Vit B, Vit C, Vit D and eicosapentaenoic acid. The addition of these exogenously added materials is intended to effect cell proliferation, cell differentiation and the synthesis, modification, and crosslinking of extracellular components.

In accordance with one embodiment the calcified material is applied directly to the implant surface in the absence of the nano-textured surface. In accordance with one embodiment apatite is applied directly to the implant surface in the absence of a nano-textured surface. Application of apatite onto the implant can be achieved using techniques known to those skilled in the art as described in U.S. Pat. Nos. 6,569,489, 6,139,585, 6,736,849 and published US Patent applications 20040153165, the disclosures of which are incorporated herein. When the apatite layer is applied directly onto the implant surface the crystals may be either in the nano- or micrometer size range. In another embodiment one or more bioactive agents are applied in the absence of a polymer matrix either directly onto the implant or onto a nano-textured surface layer prepared on the implant. Coating a prosthesis with bioactive agents can be accomplished using techniques described in U.S. Pat. No. 5,824,651, the disclosure of which is incorporated herein.

In accordance with one embodiment, lysine is added to the calcified material layer to increase the dispersion of HA particles in the collagen based bioscaffold. Addition of lysine in an amount ranging from about 0.01% to about 0.6%, and in one embodiment ranging from about 0.01% to about 0.3%, improves dispersion of HA in collagen-based matrices.

In another embodiment the metallic implant surface (with or without nano-texturing) is coated with a calcification-inducing layer, wherein the coated material does not include calcified material. In this embodiment the calcification-inducing layer comprises a biocompatible polymer and a bioactive agent. For example, in one embodiment the biocompatible polymer is in the form of a thin coating of a synthetic polymer, co-polymer, polymer network, or a mixture thereof, on the metallic implant surface, wherein the coating entraps one or more bioactive agents that will induce the regeneration of calcified tissue upon implantation into a patient. In one embodiment the biocompatible polymer comprises a collagen matrix. The calcification-inducing layer may also include one or more exogenously added biocompatible inorganic materials, biologically derived agents, or cells.

In accordance with one embodiment of the present invention a construct is provided for enhancing the attachment of soft tissue to a metal implant. More particularly, the construct allows for the creation of a differentiated transition zone at the insertion site of soft tissues (such as tendons and ligaments) into a metal prosthetic device. In one embodiment, the construct comprises a metal implant comprising a porous region, wherein said porous region exhibits a nano-textured surface. The construct is further provided with a calcified material layer, or calcification-inducing layer, that coats the nano-textured surface. This construct provides a mechanical interlocking region that binds non-metal calcified material with the metal surface by promoting a jigsaw-like union between the calcified material and the metal surface.

In accordance with one embodiment of the present invention a construct for enhancing attachment of soft tissue to a metal implant is provided, wherein the construct comprises a metal implant comprising a porous region, wherein said porous region exhibits a nano-textured surface and a naturally occurring extracellular matrix fixed to the metal implant and in contact with the nano-textured surface. In one embodiment the naturally occurring extracellular matrix is formed as fluid or gel, mixed with one or more biocompatible inorganic materials or bioactive agents and coated onto the nano-textured surface. In one embodiment the naturally occurring extracellular matrix comprises intestinal submucosa in gel form, wherein the biocompatible inorganic material or bioactive agent is dispersed within the submucosal matrix and coated and dried on the nano-textured surface.

In accordance with one embodiment a composite system for attaching soft tissue to a metal prosthesis is provided. In one embodiment the composite system comprises a five-layer composite (FIG. 1). These layers include (from implant toward soft tissue): (1) a metal prosthesis comprising a porous region, (2) a nanomaterial coating layer and/or nanosurface roughness formed on the porous region, (3) a calcified material layer in contact with the nano-textured surface, (4) a bioactive uncalcified scaffold layer bound to the calcified material layer, and (5) a cell modulating extender layer bound to the uncalcified scaffold layer. The first three layers are comprised of relatively hard and stiff composite materials, and provide the mechanical interlock to the metallic implant. The last two layers ("the cell modulating layers") are comprised of softer composites, and provide a bioactive region connecting calcified tissue to soft tissue. Within the bioactive region, both the layers typically comprise a collagen-based material. The cell modulating layers may comprise biocompatible inorganic materials and/or bioactive agents that aid in cell recruitment, proliferation, migration, differentiation, and extracellular matrix molecule synthesis and assembly. Two or more of the five aforementioned layers can be physically collapsed into one layer and can carry all the required constituents within that one layer. Further, one or more of the aforementioned layers can be eliminated as long as it does not compromise the regeneration of the differentiated soft tissue enthesis.

In accordance with one embodiment a composite bioprosthetic device is provided for replacing or repairing a diarthrodial joint. The device comprises a metal implant formed as a component for a diarthrodial prosthesis. The composite implant of the present invention can be used to attach soft tissues (including tendons, ligaments and joint capsules) to metal implants in various location including the knee, hip shoulder and spine. In one embodiment the composite construct is used to attach spinal ligaments to spinal components. In another embodiment the composite structure is used to attach a knee or hip capsule to a metal implant. In one embodiment the metal implant is formed as a tibial component for a knee joint prosthesis to allow attachment of knee joint tendons and ligaments. The metal implant is provided with a porous region located on the implant at a position where soft tissue will be attached to the prosthetic device. In one embodiment, the metal implant is further provided with a nano-texture surface on at least the portion of the metal implant that comprises the porous region. The nano-texture surface can be coated or adhered onto the metal implant using nano-sized particles and techniques known to those skilled in the art. In an alternative embodiment the nano-textured surface can be prepared by etching the surface of the implant using standard techniques known to the skilled practitioner. A calcified material layer, or a calcification-inducing layer, is bound to the nano-textured surface, with the calcified/calcifying layer being bound to a scaffold layer. The scaffold layer comprises a biocompatible polymer matrix and bioactive agents. In one embodiment only a portion of the scaffold layer is in contact with the calcified material layer/calcification-inducing layer, with the remaining unattached scaffold portion extending away from the calcified material layer/calcification-inducing layer.

The scaffold layer provides an uncalcified zone that promotes cell recruitment, proliferation, migration, differentiation, and extracellular matrix molecule synthesis and assembly. The scaffold typically comprises a biocompatible matrix that further comprises bioactive agents. In accordance with one embodiment the biocompatible matrix comprises collagen fibers.

In one embodiment the scaffold layer comprises a naturally occurring extracellular matrix, such as intestinal submucosa. The scaffold can be formed into an elongated shape (such as a rectangular structure) having two lateral side portions and two end portions, wherein the lateral side portions each have a greater length than either of the two end portions. Typically the scaffold will be seeded with cells. In accordance with one embodiment the scaffold is also embedded with one or more biologically derived agents and/or biocompatible inorganic materials. In accordance with one embodiment a first end portion of the scaffold layer is attached to the metal implant in a manner that places at least a portion of the scaffold layer in direct contact with the calcified material layer/calcification-inducing layer. The second end portion of the scaffold extends away from the calcified material layer/calcification-inducing layer.

In a further embodiment, the composite bioprosthetic device is provided with an extender layer, wherein only a portion of the extender layer is coupled to the scaffold layer. The extender layer of the bioprosthetic device functions to provide additional tissue for linking the prosthesis to the soft tissues of the patient. In one embodiment the extender comprises a naturally occurring extracellular matrix, and a synthetic portion bound to the extracellular matrix. In one embodiment the extender layer has an elongate shape, wherein one end of the extender layer is coupled the second end portion of the scaffold layer. Both the scaffold layer and the extender layer components of the composite bioprosthetic device can be formed from naturally occurring extracellular matrix such as intestinal tissue, however the extender layer further comprises a synthetic component that adds strength to the extender layer. In accordance with one embodiment the synthetic portion comprises a mesh member, and in a further embodiment the mesh member is coated with naturally occurring extracellular matrix. In one embodiment the mesh is coated with comminuted, fluidized or gelled intestinal submucosa. An extender layer suitable for use in the present invention is described in U.S. Pat. No. 6,638,312, the disclosure of which is incorporated herein.

The mesh can also be treated to enhance the hydrophilicity of the mesh and enhance its binding to hydrophilic extracellular matrices. In accordance with one embodiment the mesh is chemically treated by use of hydrolysis or by use of an amidation technique. In one embodiment the surface of the synthetic layer was treated with a gas plasma processing technique, including for example treating the surface of the synthetic layer with an ammonia plasma or an oxidative plasma.

In accordance with one embodiment the extender layer is prepared by treating a surface of a synthetic layer to increase the hydrophilicity of the surface, positioning the treated synthetic layer between a first layer of naturally occurring extracellular matrix material and a second layer of naturally occurring extracellular matrix material to make an assembly, and operating a press to exert positive pressure on the assembly. In one embodiment a pneumatic press is used to exert positive pressure on the assembly. The construct is then dried optionally while the construct is under vacuum pressure. In one embodiment the mesh comprises a bioabsorbable material selected from the group consisting of polylactic acid (PLA), polyglycolic acid (PGA), polycaprolactone (PCL), polydioxanone (PDO), trimethylene carbonate (TMC), polyvinyl alcohol (PVA), copolymers thereof, and blends thereof.

The collagen-based matrices (including the naturally occurring extracellular matrices) of the multiple layers composite prosthesis described in the present invention can be further modified to biochemically reinforce the collagen matrix. This includes the optional modification of one or more of the collagen-based matrices that comprise the calcified/calcifying inducing layer, the scaffold layer and the extender layer.

In accordance with one embodiment the extracellular matrices of the composite construct are exposed to one or more compounds that modify the structural components of the matrix to enhance the strength of the material. For example, in one embodiment, the collagen-based bioscaffold is reinforced with glycine. For example in one embodiment the collagen-based matrices are mixed with glycine at a concentration of about 0.01-0.3% wt. of the matrix material. In another embodiment the matrix material is intestinal tissue and the material is mixed with glycine at a concentration of about 0.1-0.3% wt. of the matrix material. This treatment is believed to block lysine-derived aldehydes from forming during fibrilogenesis and may increase the diameter of the collagen fibrils during enthesis regeneration.

In another embodiment the collagen based matrices are biochemically reinforced through the use of proteoglycans (PGs). Biochemical reinforcement of collagen based matrices with proteoglycans (PGs) is achieved by contacting the collagen-based matrices with one or more PGs at a concentration of about 0.01-0.1% wt of the matrix material). PGs function to promote cross linking of collagen during remodeling and thus enhance the strength of the tissue during enthesis regeneration.

In another embodiment the collagen based matrices are mixed with $MgSO_4$ and $KH_2PO_4$. As PGs are important in cross linking of collagens, the addition of $MgSO_4$ and $KH_2PO_4$ is anticipated to assist in the synthesis of PGs and thus lead to reinforcement of the matrix after implantation into a patient. In accordance with another embodiment the collagen based matrices are mixed with copper (II) sulfate pentahydrate ($CuSO_4.5H_2O$) and/or Copper (II) chloride hydrate ($CuCl_2.2H_2O$). In one embodiment these compounds are supplied at about 0.0002 to about 0.0006% of naturally occurring extracellular matrix or collagen based matrices. Cu is required for lysyl oxidase, which is involved in extracellular cross linking of collagens during remodeling of naturally occurring extracellular matrices, such as intestinal submucosa. $SO_4^{-2}$ is anticipated to contribute to synthesis of new proteoglycans/GAGs.

In another embodiment the collagen based matrices are mixed with $Fe^{+2}$, $Mn^{+2}$ and $Ca^{+2}$. Mixing collagen based matrices (including a naturally occurring extracellular matrix) with $Fe^{+2}$, $Mn^{+2}$ and/or $Ca^{+2}$ may enhance the post-translational modifications of collagen during remodeling. Iron ($Fe^{+2}$) is supplied, in accordance with one embodiment, at about 30 to about 60 mg/kg of the collagen based matrix by iron-dextran and/or iron (II) sulfate heptahydrate ($FeSO_4.7H_2O$). Manganese ($Mn^{+2}$) is supplied, in accordance with one embodiment, at about 0.0003 to about 0.0009% of the collagen based matrix by manganese (II) sulfate monohydrate ($MnSO_4$, $H_2O$). In addition, in one embodiment, supplementing the collagen based matrices with Vit A, Vit B complex, Vit C and Vit D is anticipated to have positive effects on collagen production during remodeling. It is believed that vitamin A plays a role in cell differentiation and skeletal development, and vitamin D plays a role in cell growth, differentiation and bone mineralization. It is also believed that all these vitamins play a role in collagen formation during remodeling of collagen based matrices, including, for example, the remodeling of naturally occurring extracellular matrices. The collagen based matrices may also be supplemented with eicosapentaenoic acid. Supplementing the collagen based matrices with eicosapentaenoic acid is anticipated to have positive effect on tendon wound healing and collagen production during remodeling.

The present invention also provides a method of attaching soft tissue to a metal implant. The method comprises the steps of providing a metal implant construct, wherein the construct comprises: 1) a metal implant comprising a porous region, wherein said porous region exhibits a nano-textured surface and 2) a biocompatible polymer matrix coating the nano-textured surface, wherein the polymer matrix comprises a naturally occurring extracellular matrix with exogenously added biocompatible inorganic materials distributed within the matrix. The biocompatible polymer matrix that coats the nano-textured surface is then contacted with at least a portion of a scaffold layer, wherein the scaffold layer comprises a biocompatible polymer matrix and a biocompatible inorganic material, and optionally, bioactive agents and exogenously added cells and/or biologically derived agents. In one embodiment the scaffold layer comprises a naturally occurring extracellular matrix, such as intestinal submucosa. A portion of the scaffold layer is then attached to the proximal end of an extender portion, wherein the extender portion comprises a naturally occurring extracellular matrix, and a synthetic portion coupled to the naturally occurring extracellular matrix. In one embodiment the synthetic portion comprises a mesh member wherein said mesh member is coated with comminuted submucosa-derived matrix. Upon implantation into a patient, the distal end of the extender portion is attached to a patient's soft tissue.

In another embodiment, the extender comprises a naturally occurring extracellular matrix as a top tissue layer that is coupled to a bottom tissue layer of naturally occurring extracellular matrix, wherein the synthetic portion is coupled to and positioned to lie between the top tissue layer and the bottom tissue layer. In a further embodiment the extender comprises multiple sections of a submucosal matrix, each separated by a synthetic portion and in one embodiment each section of submucosal matrix includes multiple layers of submucosal matrix. In one embodiment the submucosal matrix of the extender is intestinal submucosa. In one embodiment the synthetic portion comprises a biocompatible polymer. In one embodiment the synthetic portion comprises a synthetic biocompatible polymer (for example a material selected from the group consisting of Prolene™, Vicryl™, and Mersilene™ and Panacryl™). In accordance with one embodiment, the synthetic portion includes a mesh member coupled to at least one section of the naturally occurring extracellular matrix, and in one embodiment the mesh member is bioabsorbable. In another embodiment the mesh member further comprises a layer of comminuted, fluidized or gelled naturally occurring extracellular matrix coating the mesh.

The present invention also provides a kit for repairing a diarthrodial joint, said kit comprising a metal implant construct, a scaffold comprising a biocompatible polymer matrix and a biocompatible inorganic material and optionally bioactive agents and exogenously added cells and/or biologically derived agents; and an extender graft comprising a naturally occurring extracellular matrix, and a synthetic portion coupled to the naturally occurring extracellular matrix, said synthetic portion including a mesh member wherein said mesh member is optionally coated with comminuted naturally occurring extracellular matrix. More particularly, the metal implant construct comprises a metal implant that includes a porous region, wherein the porous region exhibits a nano-textured surface, and a biocompatible polymer matrix coating the nano-textured surface. In one embodiment the biocompatible polymer matrix comprises intestinal submucosa with exogenously added biocompatible inorganic materials or bioactive agents distributed within the matrix. In another embodiment the biocompatible polymer matrix comprises a synthetic biocompatible polymer coating coupled with a bioactive agent. In yet another embodiment a biocompatible inorganic material and/or bioactive agent is directly coupled to the nano-textured surface without a biocompatible polymer matrix. In one embodiment the biocompatible inorganic material is hydroxyapatite, optionally co-deposited with a bioactive agent, directly onto the nano-textured surface without a biocompatible polymer matrix. The kit can be used to implant the metal prosthetic device in the patient and attach soft tissues to the metal prosthesis by attaching the scaffold component to the metal implant construct (in a manner that places the porous implant surface with or without it's biocompatible polymer matrix coating in direct contact with the scaffold) and attaching one end of the extender to the scaffold and attaching the other end of the extender to the soft tissue of the patient.

What is claimed is:

1. A composite bioprosthetic comprising
   a metal implant that comprises a porous region, wherein the porous region exhibits a nano-textured surface;
   a calcified material layer coating the nano-textured surface; and
   a scaffold layer comprising a biocompatible polymer matrix and growth factors, wherein at least a portion of the scaffold layer is in contact with the calcified material layer.

2. The composite bioprosthetic of claim 1 wherein the calcified material layer consists essentially of nano-scale hydroxyapatite particles.

3. The composite bioprosthetic of claim 1 wherein the calcified material layer comprises hydroxyapatite and a biocompatible polymer matrix.

4. The composite bioprosthetic of claim 3 wherein the calcified material layer further comprises an exogenously added bioactive agent.

5. The composite bioprosthetic of claim 1 wherein the calcified material layer comprises a naturally occurring extracellular matrix and exogenously added biocompatible inorganic material selected from the group consisting of hydroxyapatite, calcium phosphate, alpha-tricalcium phosphate, beta-tricalcium phosphate, calcium carbonate, barium carbonate, calcium sulfate, barium sulfate, polymorphs of calcium phosphate, sintered and non-sintered ceramic particles.

6. The composite bioprosthetic of claim 1 wherein the scaffold layer comprises a submucosal matrix.

7. A composite bioprosthetic comprising
   a metal implant that comprises a porous region, wherein the porous region exhibits a nano-textured surface;
   a calcified material layer coating the nano-textured surface; and
   a scaffold layer comprising a biocompatible polymer matrix and growth factors, wherein at least a portion of the scaffold layer is in contact with the calcified material layer; and
   an extender layer coupled to the scaffold layer, the extender layer comprising a submucosal matrix, and a synthetic mesh member coupled to the submucosal matrix.

8. The composite bioprosthetic of claim 7 wherein the submucosal matrix comprises intestinal submucosa.

9. The composite bioprosthetic of claim 8 wherein the submucosal matrix of the scaffold layer further comprises a compound selected from the group consisting of copper (II) sulfate pentahydrate ($CuSO_4 \cdot 5H_2O$), copper (II) chloride hydrate ($CuCl_2 \cdot 2H_2O$), iron-dextran, iron (II) sulfate heptahydrate ($FeSO_4 \cdot 7H_2O$), manganese (II) sulfate monohydrate ($MnSO_4, H_2O$), magnesium sulfate heptahydrate ($MgSO_4 \cdot 7H_2O$), magnesium phosphate dibasic trihydrate ($MgHPO_4 \cdot 3H_2O$), glycine, proteoglycans, Vit A, Vit B, Vit C, Vit D and eicosapentaenoic acid.

\* \* \* \* \*